United States Patent [19]

Yoshida

[11] Patent Number: 4,692,800
[45] Date of Patent: Sep. 8, 1987

[54] AUTOMATIC INSPECTION DEVICE

[75] Inventor: Hajime Yoshida, Tokyo, Japan

[73] Assignee: Hajime Industries Ltd., Tokyo, Japan

[21] Appl. No.: 772,759

[22] Filed: Sep. 5, 1985

[30] Foreign Application Priority Data

Nov. 22, 1984 [JP] Japan ............................ 59-247743

[51] Int. Cl.$^4$ ........................................... H04N 7/18
[52] U.S. Cl. ................................. 358/106; 358/101
[58] Field of Search ............... 358/107, 101, 106, 153, 358/22; 356/390; 250/563, 572; 382/8, 42

[56] References Cited

U.S. PATENT DOCUMENTS

| 4,345,312 | 8/1982 | Yasuye et al. | 358/106 X |
| 4,352,125 | 9/1982 | Guth | 358/106 X |
| 4,484,542 | 6/1984 | Miyazawa | 358/106 |
| 4,532,650 | 7/1985 | Wihl et al. | 358/106 X |

FOREIGN PATENT DOCUMENTS 0096088  5/1985  Japan .................................. 358/106

Primary Examiner—James J. Groody
Assistant Examiner—Victor R. Kostak
Attorney, Agent, or Firm—Murray Schaffer

[57] ABSTRACT

An object to be inspected is illuminated and its image is picked up by an optical image sensor which provides a video signal thereof. The optical image is divided into at least two portions which are mutually symmetrical to each other, and the specific video signals of corresponding parts of the mutually symmetrical portions are compared sequentially to thereby determine whether the object has a defect or not.

8 Claims, 13 Drawing Figures

AUTOMATIC INSPECTION DEVICE

BACKGROUND OF THE INVENTION

1. Field of the Invention

The present invention relates generally to a method for automatically inspecting an object and to an apparatus for performing the method, and more particularly to an automatic inspection method and apparatus for determining defects in products or components by the use of an optical image sensor rather than by measurement of absolute dimensions or the like.

2. Description of the Prior Art

Various types of automatic inspection devices have been proposed and utilized to replace the visual inspection of products or components by a human inspector. Conventional devices use optical image sensors such as, for instance, a television camera to photosense the products or components and then by processing the image signals therefrom in a data processor such as a computer or the like, determine the shape, dimension, surface defects, etc. of the product.

Several examples of the automatic inspection devices according to the conventional art will be explained with reference to FIGS. 1, 2, and 3. In the example of FIG. 1, 1 designates a television camera, 2 an electronic processor such as a computer or the like which processes the video signals from the television camera 1; 3 and 3A, respectively, designate light sources for illuminating purposes; 4, 4A, 5 and 5A reflection mirrors; 7 and object to be inspected such as products or components, and 6 a standard body for the object to be inspected that has no defects. The images of the standard body 6 and of the object 7 being inspected, as illuminated by light sources 3, 3A respectively, are received by the television camera 1 being introduced therein in overlapping relationship brought about by the combinations of reflection mirrors 4, 4A and 5, 5A, respectively. If the shape or patterns of the standard body 6 and inspected object 7 are entirely coincident with each other, the inspected object 7 is deemed to be good and the processor 2 does not deliver any output signal, but if there is a difference between the two, even in one part, the inspected object 7 is deemed to have a defect and the processor 2 delivers a defect signal.

In other words, the conventional example shown on FIG. 1 constitutes an inspection method where the standard object 6 and the inspected object 7 are placed at separate locations while they are illuminated with separate light sources, respectively. The two images are overlapped by utilizing the mirrors, and they are inspected by determining whether the two images are matched or not.

In the other conventional example as shown on FIG. 2, it is assumed that the object 7 to be inspected has a pattern which consists of a black coloured portion 7A and a transparent portion 7B, whereas a standard object 8 has a standard pattern such as a negative picture against the inspected object 7 which is a pattern that is opposite the black portion 8A and transparent portion 8B to the inspected object 7. In FIG. 2, 9 designates a reflection mirror that is located at the opposite side of the standard object 8, from the object 7 being inspected. In this case, the inspected object 7 and standard object 8 are arranged so that they are on the same axis to the optical axis of the television camera 1, which is itself located at the side of the inspected object 7 and that the standard object 8 keeps its standard pattern in a faithful positive to negative relation against the inspected object 7. In such case, if the pattern of the inspected object 7 shows a truly positive to negative relation to the negative standard pattern of the standard object 8 (if there are not defects), the light from the light source 3 which is placed between the camera and the object 7 does not pass both patterns and is not reflected by reflector 9 and hence does not enter the television camera 1. However, if there is a defect in the pattern of the object 7, the light will reach the reflection plate 9 through the defect and then be reflected to the television camera 1 so that the processor 2 that receives the video signal therefrom will judge that there is a defect and thereby deliver a defect signal.

Further, as another example of the prior art, as shown in FIG. 3, there is a method in practice that judges the good or bad of the inspected object 7 by comparing the pattern of the inspected object 7 as photosensed by television camera 1 or the like with a memorized standard pattern as readily stored in the memory of the computer 2A that is used as the processor.

As will be understood from the first and second examples as described above, both conventional defect inspection methods require some kind of a standard subject against which the inspected object is to be compared. In the third example, as shown on FIG. 3, a pattern of the standard object is memorized in the memory of the computer which pattern is to be compared to the pattern from television camera 1, as it picks up the inspected object. Therefore, the requirement of a standard pattern cannot be disregarded for this third case.

OBJECTS AND SUMMARY OF THE INVENTION

Accordingly, it is an object of the present invention to provide a method and apparatus which can automatically detect a defect in an object being inspected without utilizing any standard object.

It is another object of the invention to provide a method and apparatus in which the optical image of an object being inspected as received by an optical image sensor is divided into at least two mutually symmetric portions and the image signals from the coresponding parts of the symmetric portions are sequentially compared to thereby determine whether the object has a defect or not.

DESCRIPTION OF THE PREFERRED EMBODIMENTS

Figure 1:
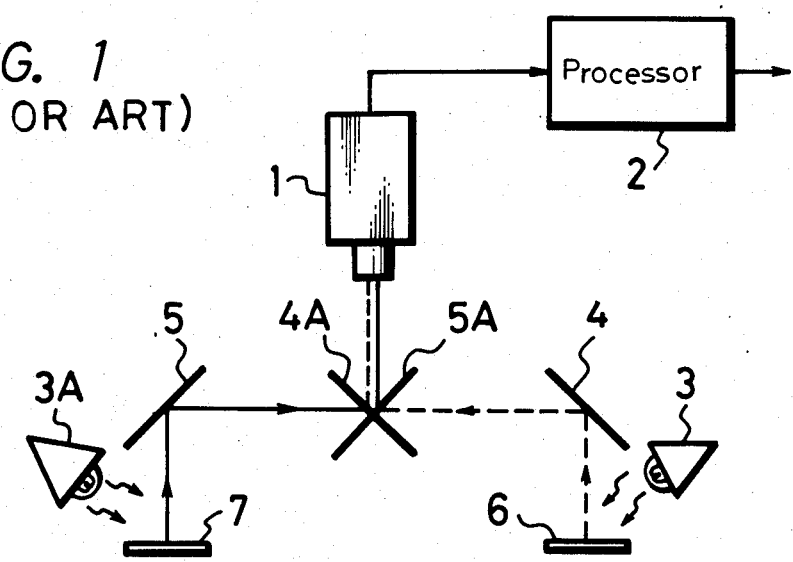
FIGS. 1, 2 and 3 are schematic views, respectively, showing prior art automatic inspection device.
Figure 2:
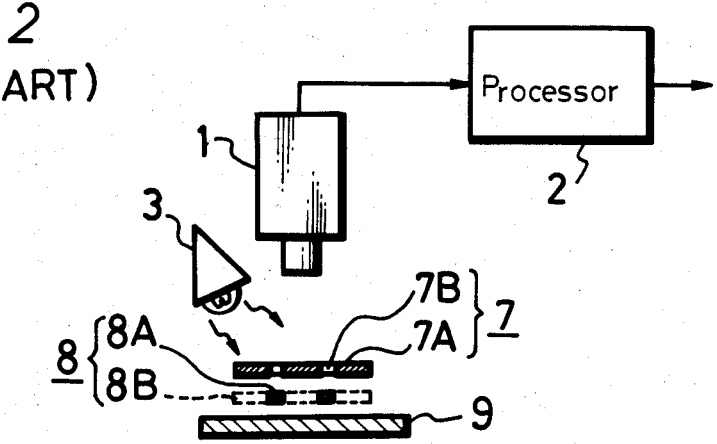
Figure 3:
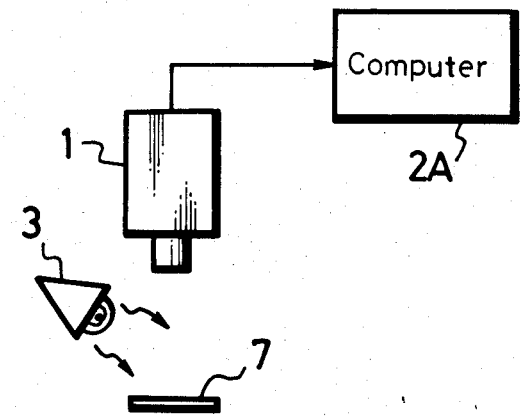
Figure 4A:
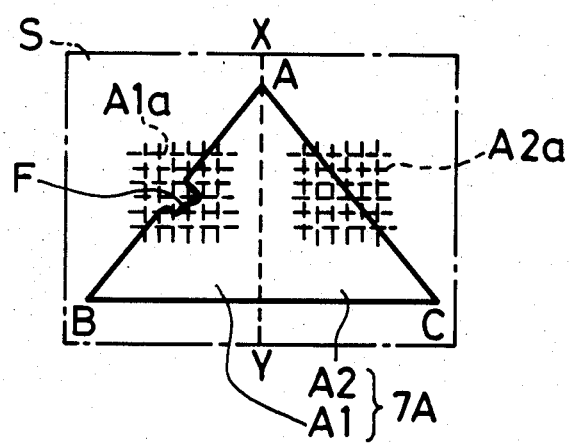
FIGS. 4A–4E is a schematic diagram illustrating the basic theory of the present invention.
Figure 4B:
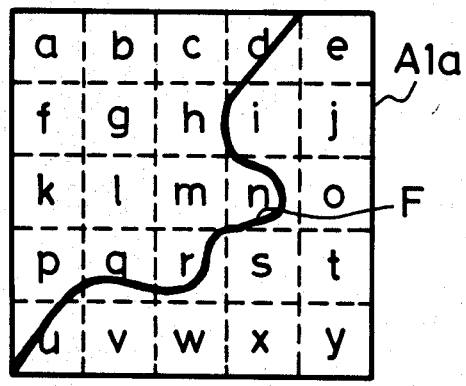
Figure 4C:
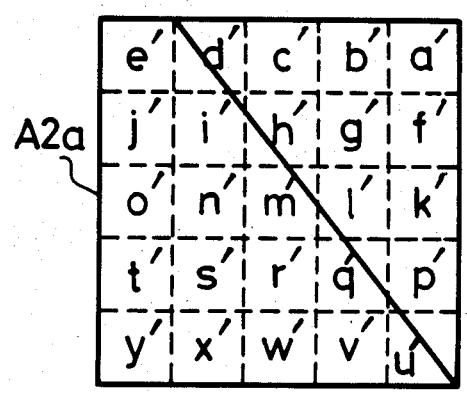

The present invention will be explained hereunder with reference to FIGS. 4A to 4C. FIG. 4A shows an optical image 7A of an object being inspected (not shown) on the target screen or the photoelectric conversion screen S of a television camera photosensing the object. In this case, the shape of the object is, for example, an isosceles triangle ABC as shown in FIG. 4A. The target screen S is split into two by a line X-Y that passes through the apex point A of the isosceles triangle ABC, and, therefore, the optical image 7A of the isosceles triangle is divided into portion A1 and A2. The line X-Y is selected and arranged so that portions A1 and A2 are symmetrical (A2=A1) with each other, with respect to the line X-Y. Thus, each of the portions A2 and A1 becomes a standard mutually comparable against each other. Therefore, if the electric signals of the corresponding parts of the portions A1 and A2 from the television camera are compared sequentially, the defects and the like variations in the inspected object may be determined. That is, if there are no abnormalities or defects in both portions A1 and A2, the two signals of the corresponding parts of both portions A1 and A2 from the television camera are the same and the inspected object is a good product, whereas, if both of the signals are not the same, the inspected object is deemed a reject.

One example of the comparison of both portions A1 and A2 will be explained. For instance, the target screen S of the television camera is formed of a number of equally fine picture elements (pixels) arranged in a mesh pattern (as explained later, the image signals from the television camera are processed as such by an electronic processor or the like), and the degree of brightness of the optical images of the inspected object projected on the corresponding picture elements of both the portions A1 and A2 are converted to electrical signals. The corresponding electrical signals are then compared to each other to thereby compare both the portions A1 and A2. This will be explained by citing partial shape comparison of, for instance, line AB and line AC of the triangle shown on FIG. 4A. Further, it shall be assumed that while line AC is complete, line AB contains a defect F as shown on the drawing. Further, as mentioned above, because the target screen S of the television camera is formed of many fine picture elements both the small part A1a of portion A1, containing the defect F, and the corresponding small part A2a of portion A2 contain more than one picture element, as seen magnified in FIG. 4B and 4C. Also in the same figures, the picture elements of part A1a arranged in a mesh-like manner are taken in sequence as a, b, c, - - - w, x, y and the corresponding picture elements of the corresponding part A2a are taken in sequence (mirror image) as a', b', c', - - - w', x', y', with respect to line X-Y.

The electrical signals from the corresponding picture elements a - - - y and a' - - - y' of both parts A1a, A2a are consecutively compared. Since the portion of the inspected object that is projected on the picture elements n, r and g of part A1a contains the edge of the defect F, there are differences between each of the electrical signals from these picture elements n, r and q as well as from the electrical signals of the neighboring picture elements h, l and m when compared to the electrical signals from the corresponding picture elements n', r' and q' as well as the electrical signals of the picture elements h', l' and m' of section A2a. Therefore, it is possible to detect that line AB and line AC are different, and once this detection has been made to determine that the inspected object is a defective product.

Figure 5:
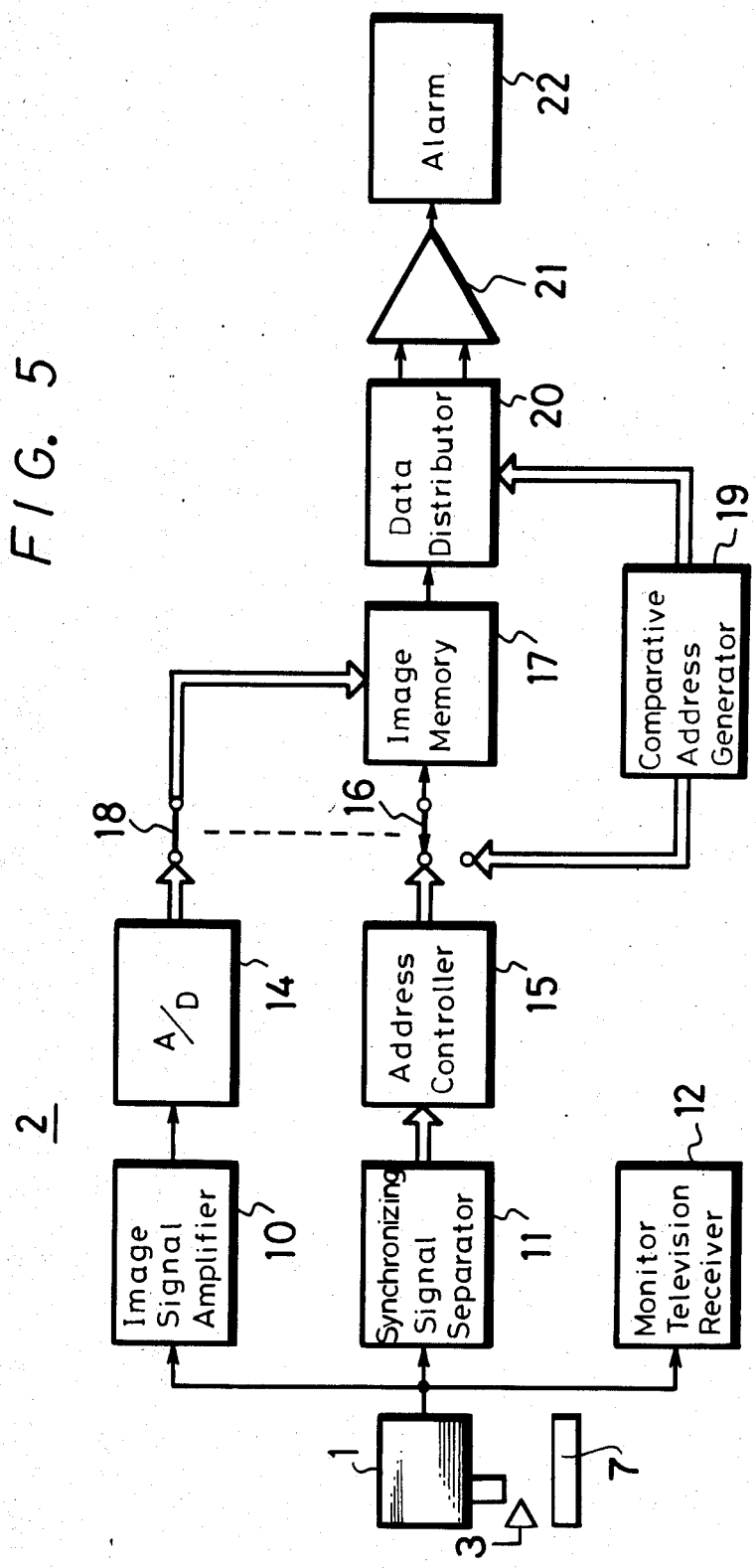
FIG. 5 is a block diagram of an automatic inspection apparatus embodying the present invention.

A practical embodiment of the invention that carries out the above mentioned method of inspection is illustrated with reference to FIG. 5. In FIG. 5, the image signal of the object 7 as illuminated by the light source 3 is picked up by the television camera 1, which is the optical image sensor, and is simultaneously supplied to an image signal amplifier 10, a synchronizing (sync.) signal separator 11 and a television monitor 12 being part of the electronic circuitry of a processor such as mentioned above and here generally referred to by the numeral 2a. The image signal amplifier 10 supplies an amplified image signal to an A/D (analog to digital) converter 14 in which the analog image signal is converted into a digital signal. The sync. signal separator 11 separates and delivers vertical sync. and horizontal sync. signals from the composite image signal. The separator may be contained readily within the television camera 1, and, therefore, a separate sync. signal separator 11 is not generally necessary. The television monitor 12 is used to check whether the inspected object 7 is at the correct position within the visual field of the television camera 1, or to confirm that the inspected object is picked up by the television camera 1 in proper focus and so on.

The vertical sync. signal and horizontal sync. signal separated by the sync. signal separator 11 are supplied to an address controller 15. This address controller 15 supplies address signals, that are synchronized to both the vertical and horizontal sync. signals through a switch 16, to the address input terminal of an image memory 17. On the other hand, the digitalized image signal from the A/D converter 14 is supplied to the image memory 17 through an on-off switch 18 that is ganged with switch 16. At the timing of the above two sync. signals, that is, the timing of the address signals, the digitalized image signal is stored in the image memory 17 being arranged in proper sequence. As such, one frame of the digitalized image signals of the inspected object is memorized into image memory 17 with a constant arrangement. Such memory devices as herein described are readily available on the market as image frame memories and hence it would be unnecessary to go into details at this occasion.

Further, in FIG. 5, 19 designates a comparative address generator which consecutively generates the address signals for the parts within the image that are to be compared, 20 is a data distributor to which both outputs from the image memory 17 and comparative address generator 19 are supplied, and 21 denotes a digital comparator which compares the two output data from the data distributor 20.

In the operation of the processor 2a, the image signal of the inspected object is first converted into the digital signal by the A/D converter 14 and then one frame thereof is stored in the image memory 17. Thereafter, the on-off switch 18 and switch 16 are changed over in ganged relation to the positions opposite to those shown in FIG. 5 (i.e., open). The supply of the signal to the image memory 17 from A/D converter 14 is then stopped. On the other hand, at this time, the address input terminal of the image memory 17 is changed and is connected to the address signal output terminal of the comparative address generator 19 through the switch 16, so that at this time, the address signals that respectively correspond to the parts in the aforementioned image that are to be compared from the comparative address generator 19 are consecutively supplied to image memory 17. Such address signals from the comparative address generator 19 are the address signals corresponding to respective pair of picture elements a, a'; b, b'; - - - y; y' in the case of, for instance, FIGS. 4B and 4C.

Thus, after the switches 16 and 18 are changed over, the digitalized image signals as stored in image memory 17 are consecutively delivered to the data distributor 20 in the aforementioned sequence, which is to say, in accordance with the address signals from the comparative address generator 19. After the address signals for the two parts that are to be compared, for instance, the two address signals for the first pair of parts a and a' are supplied to the image memory 17, the comparative address generator 19 supplies a command signal to the data distributor 20 to deliver therefrom the data that correspond to picture elements a and a'. Then, the data distributor 20 simultaneously supplies the data (digitalized image signals) of picture elements a and a' as delivered from the image memory 17, respectively to the input terminals of the digital comparator 21. Since, for example, the two data of picture elements a and a' are supplied to the data distributor 20 in sequence, this data distributor 20 comprises logic circuitry, for instance, latches or shift registers or the like that have memory functions. Comparator 21 then compares the two data, and if there is a difference therebetween (which corresponds to the case when the inspected object has a defect), it delivers a signal. By such signal, it is possible to activate, for example, an alarm 22 to notify that a defect exists in the inspected object, or when the inspection is conducted on objects that are transferred on a conveyor or the like although not indicated in the figure, a defect product rejection means (not shown) may be activated to remove the defect object from the conveyor. The embodiment of the invention shown in FIG. 5 is used to inspect a simple shaped object such as shown in FIG. 4A, for instance, However, even when the shape of the inspected object is complicated, only minor changes or modifications in the circuitry may be required.

Further, the example illustrated in FIG. 5 is solely an example used to plainly and easily explain the concepts of the present invention.

In addition, without using the specific construction as shown in FIG. 5, the present invention can be more easily realized by operating a single cpu (central processing unit) by making the proper software, which not only is technically feasible to one skilled in the art, but which may be easily put into practice. At the same time, the schematic diagram of FIG. 5 used to explain the concept is sufficient so that one who wishes to practice the invention may refer to it in making a practical software program.

As for computers, the recent micro computer functions have been greatly improved, and the cost thereof has been so reduced that at present an electronic engineer having normal technical knowledge may easily make the necessary software making, so that the practice of the present invention becomes very easy. For instance, the setup of image areas that should be mutually compared may be preset in the software and program making stage, or may be preset by an external keyboard or a light pen for each operation. It is apparent that the user may easily select the design to fit the application purposes and may freely apply such setup to suit each occasion.

Figure 4D:
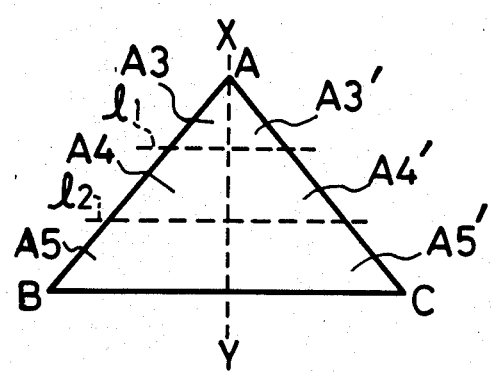

Further, when more precise defect inspection of the object is desired, that is to say, when there is a desire to inspect by comparing mutual image portions as finely divided, for instance, as shown on FIG. 4D, the inside area of the triangle ABC such as that shown in FIG. 4A, may be further divided by two horizontal lines 11, 12 which are respectively perpendicular to the line X-Y. In this manner, the number of picture elements arranged in the mesh pattern may be increased. For instance, the number of symmetrical sections A3, A3'; A4, A4'; and A5, A5' may be formed so that A3=A3'N, A4=A4', A5=A5' is satisfied, whereby sequential comparison of the symmetrical section may be made in the same manner as aforedescribed. In this case, there is the advantage that the precise location of the defect in the object can be readily determined.

The method of image division need not necessarily be the way it is shown in FIGS. 4A or 4D, but depending upon the shape of the inspected objects shape, or the precision required, they may be modified, so long as the division is made to form respective symmetrical shaped sections in the image of the object.

Figure 4E:
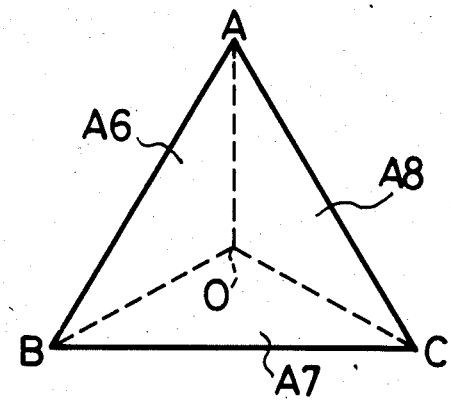

For instance, FIG. 4E shows such an example, wherein the inspected objects' shape is a regular triangle. Here lines may be drawn from its center O to each of the points or apexes A, B, C to divide the triangle into three mutually symmetrical portions A6, A7 and A8, where A6=A7=A8. Thus, sections are established so that the same type inspection judgement as aforementioned can be made.

Futher, the method to divide the target screen S, as explained with reference with FIG. 4A, may be modified so that the picture elements need not be necessarily limited to the mesh-like arrangements. For example, it may be possible to compare the distances from the lines AB and AC of both parts A1 and A2 to the line X-Y, in other words, the distances from line X-Y to the outlines of both halves of the ABC triangle, which is the inspected object.

Figure 6A:
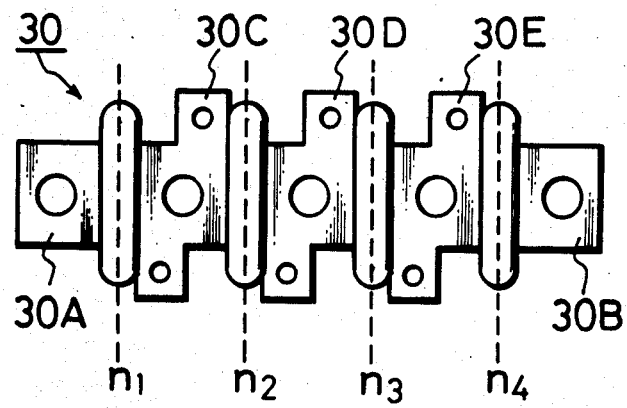
FIGS. 6A, 6B and 7A, 7B are schematic diagrams, respectively, showing objects being inspected for defects in accord with the present invention.
Figure 6B:
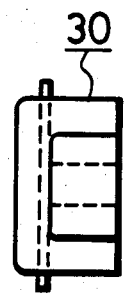

As a next step, examples of image division for real industrial products (for example, electronic components) are shown on FIG. 6 and FIG. 7 as practical cases in reference. FIG. 6 shows a terminal board or base 30 that is used to connect electric circuits. FIG. 6A is its top view and FIG. 6B is its side view. In these figures, 30A, 30B indicate parts of the terminal board 30 that are made of insulating material (normally plastics) while 30C, 30D and 30E show terminal plates made of metal material, respectively. If the terminal board 30 is divided by broken lines n1, n2, n3 and n4 which are parallel to one another as in FIG. 6A, respective parts satisfy the requirement for forming equal sections, e.g., 30A=30B and also 30C=30D=30E. Therefore, by making two comparison inspections as earlier disclosed, defect inspection of the terminal board 30 may be conducted.

Figure 7A:
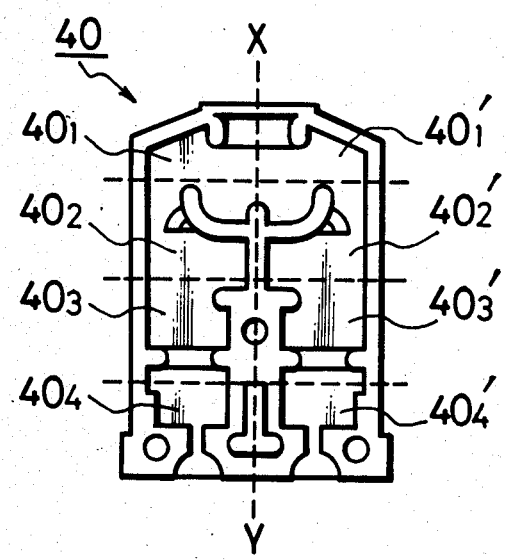
Figure 7B:

FIG. 7A shows the complex inside construction of the insulating body (normally made of plastics) of a power plug 40 which is used for connection of home appliances to a power source (100 V-240 V) and FIG. 7B is the side view of the power plug 40. By adopting a similar division method as those in FIGS. 4A, 4D, 4E, as well as FIG. 6, the power plug 40 is divided into mutually symmetrical parts such as 401, 40'1, 402, 40'2; 403, 40'3; and 404, 40'4 with respect to line X-Y and hence corresponding parts 401=40'1; 403=40'3; and 404=40'4, and so forth are made. Then, if the corresponding parts are respectively compared in the same manner as aforementioned, the inspection of this object for defects 40 can be simply conducted.

Without escaping from the scope of the divided comparison inspection method of the present invention, it is apparent that it can apply not only for the above listed electronic components and the like, but can be applied also to numerous other items by any one skilled in the art who may also provide many variations and changes, so that the scope of the invention should be determined by the appended claims only.

As mentioned above, according to the present invention, since no standard for the object to be inspected is used, the image of the inspected object is divided properly to provide divided portions one of which will be a standard for other divided portions and the corresponding parts thereof are compared to inspect whether or not the object has any defect, the inspection becomes simple.

In this invention, it is the premise that the object to be inspected includes mutually symmetrical and/or equal portions, if properly divided, which could be compared. In general goods, industrial products, components thereof and so on, there are many products which satisfy the above premise and hence there are many products to which the present invention can be applied.

Although the present invention has the above premise, the present invention can be easily carried out in practice and the construction of the apparatus is simple so that the inspection apparatus of the invention can be provided at low cost.

Further, since the invention can be operated simply and its application is wide, the present invention is very effective.

I claim:

1. A method of automatically inspecting an object, comprising the steps of:
   (a) illuminating the object to be inspected;
   (b) viewing said object with a single optical image sensor having a target screen which includes a number of picture elements arranged in a mesh pattern to provide an optical image thereof in the form of a video signal;
   (c) dividing the optical image of said object received by said sensor into at least two portions which are mutually symmetrical to each other with respect to a line or point; and
   (d) comparing sequentially video signals from each of the picture elements at corresponding positions in specifically corresponding parts of said mutually symmetrical portions sequentially with respect to the line or point to thereby determine whether said object has a defect or not.

2. The method according to claim 1 including the step of converting said video signals into digital video signals.

3. The method according to claim 2, wherein said step for dividing said optical image comprises sequentially storing the digital video signal of said object in a memory synchronously with a synchronizing signal contained in said video signal, simultaneously extracting from the digital video signal stored in said memory the specific digital video signals of the corresponding parts of said at least two portions, and comparing said specific signals.

4. An automatic object inspection apparatus comprising a light source illuminating said object, a single optical image sensor having a target screen which includes a number of picture elements arranged in a mesh pattern and producing a video signal of said optical image and an electronic processor for determining whether said object has a defect or not, said electronic processor comprising:
   (a) means for dividing said optical image into at least two portions which are symmetrical to each other with respect to a line or point; and
   (b) means for sequentially comparing the video signals of each picture element at corresponding positions in specific corresponding parts of said two symmetrical portions with respect to a predetermined line or point to determine the differences therein.

5. The apparatus according to claim 4, wherein said optical image dividing means includes means for converting the video signal from said optical image sensor into a digital video signal, means for storing the digital video signal in synchronism with vertical and horizontal synchronizing signals contained in the output of said optical image sensor, and means for simultaneously deriving the digital video signals of corresponding parts of said two portions.

6. An automatic object inspection apparatus comprising a light for illuminating the object, a single optical image sensor having a target screen which includes a number of picture elements arranged in a mesh pattern and producing a video signal of said optical image, and an electronic processor for determining whether said object has a defect or not, said electronic processor comprising:
   (a) converting means for converting the video signal from said optical image sensor into a digital video signal;
   (b) separating means for separating vertical and horizontal synchronizing signals from the video signal of said optical image sensor;
   (c) address signal generating means for generating an address signal in synchronism with the vertical and horizontal synchronizing signals from said synchronizing signal separating means;
   (d) memory means for memorizing the digital video signal from said converting means in sequence with the timing of said address signal from said address signal generating means;
   (e) comparative address signal generating means for generating a comparative address signal and a command signal;
   (f) switching means for selectively supplying one of said address signal and said comparative address signal to said memory means;
   (g) distributor means for sequentially receiving the digital video signal from said memory means based upon said comparative address signal and delivering simultaneous digital video signals of corresponding parts of at least two portions of said optical image which are mutually symmetrical to each other with respect a line or point, in accordance with said command signal; and
   (h) comparing means for comparing the digital video signals from said distributor means to thereby inspect said object, wherein when said object has a flaw, said comparing means produces a defect signal, while when said object has no flaw, said comparing means produces no output signal.

7. The apparatus according to claim 6 including a television monitor for receiving the video signal from said optical image sensor and reproducing thereon an image of said object.

8. The apparatus according to claim 6 includes means for producing an alarm when a defect signal occurs.